United States Patent [19]

Schnell

[11] Patent Number: 4,983,178
[45] Date of Patent: Jan. 8, 1991

[54] LANCING DEVICE

[75] Inventor: William J. Schnell, Libertyville, Ill.

[73] Assignee: Invictus, Inc., Chicago, Ill.

[21] Appl. No.: 270,077

[22] Filed: Nov. 14, 1988

[51] Int. Cl.⁵ ............................................. A61B 17/32
[52] U.S. Cl. .................................................... 606/181
[58] Field of Search ................... 128/314, 329 R, 760, 128/770; 604/46, 47, 22, 156, 157; 606/181, 182

[56] References Cited

U.S. PATENT DOCUMENTS

| | | | |
|---|---|---|---|
| 3,659,608 | 5/1972 | Perry | 128/314 |
| 3,760,809 | 9/1973 | Campbell | 1238/314 |
| 3,901,243 | 8/1975 | Read | 128/329 R |
| 4,452,243 | 6/1984 | Leopoldi et al. | 128/329 R |
| 4,539,988 | 9/1985 | Shirley et al. | 128/314 |
| 4,715,374 | 12/1987 | Maggio | 128/314 |

Primary Examiner—Max Hindenburg
Attorney, Agent, or Firm—Garrettson Ellis

[57] ABSTRACT

An integrated lancing device comprises a generally U-shaped spring member defining a pair of arms having free ends. A lance blade is carried in transverse position on one of the arms adjacent the free end, the one arm defining a trigger projection typically positioned substantially along the axis of the one arm. The other of the pair of arms carries a trigger member as an integral part thereof, with the trigger member extending toward the trigger projection. The arms may be flexed outwardly into a cocked position and held there by engagement of the trigger projection and trigger member. The integrated lacing device may be triggered to cause the arms to suddenly flex together, causing the lance to strike a part of a patient.

16 Claims, 2 Drawing Sheets

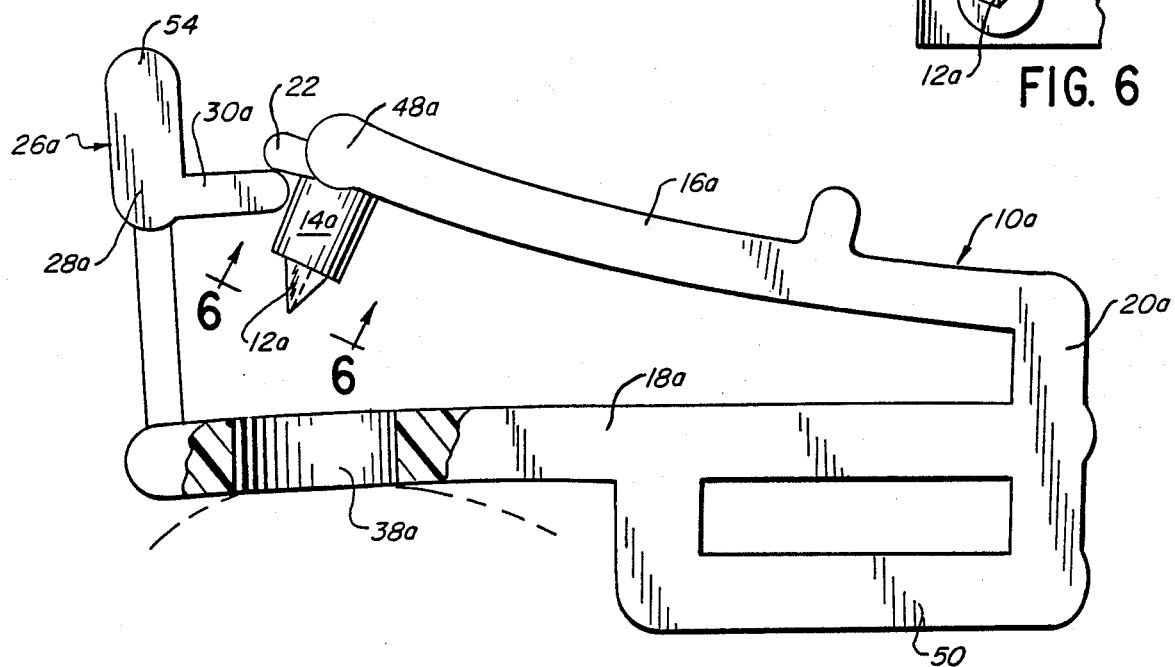
FIG. 4
FIG. 6
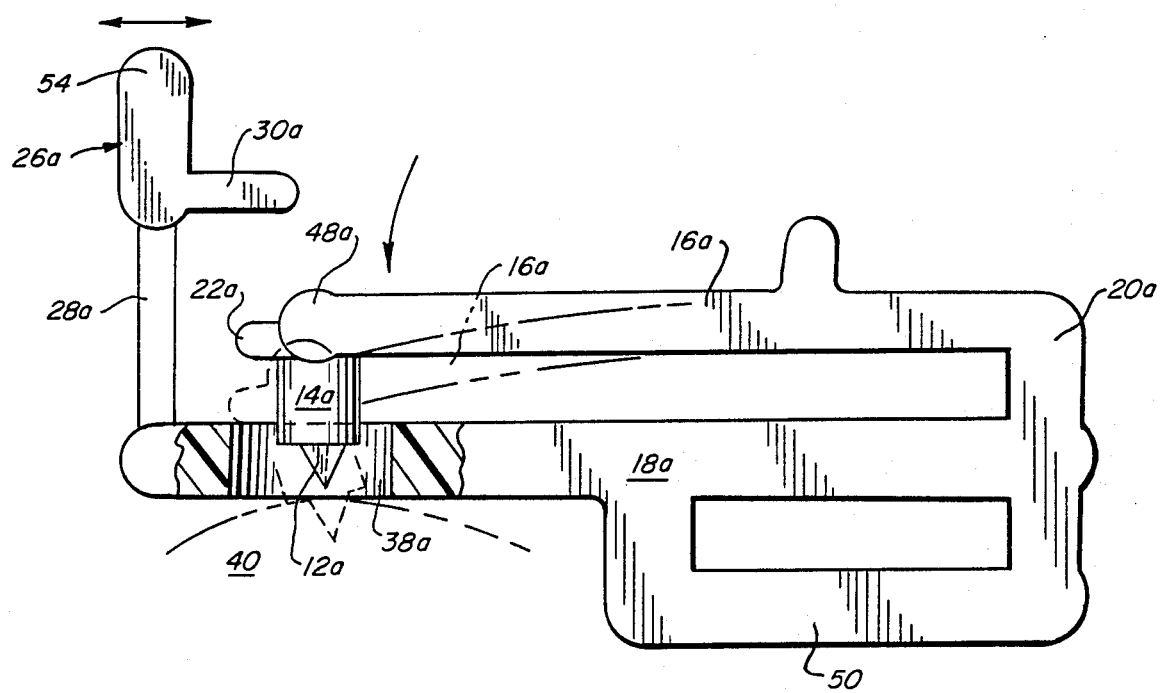
FIG. 5

LANCING DEVICE

BACKGROUND OF THE INVENTION

Automatic surgical lancing devices of various kinds are known to the art, primarily for the use of permitting a patient to draw a sample of his own blood. To accomplish this, it is generally required with respect to most people to provide an automatic means for driving the lancet into the finger. Lancing devices are also used in the clinical setting, where a care giver draws blood samples from several patients. To assure a sterile procedure, it is desirable for the automatic lancing devices to be cheap enough for one-time use, to avoid transmission of any infection by a second use.

Examples of integrated surgical lancing devices in the prior art include those described in Shirley et al. U.S. Pat. No. 4,539,988; Maggio U.S. Pat. No. 4,715,374; and Campbell, Jr. U.S. Pat. No. 3,760,809. Additionally, Munsch et al. U.S. Ser. No. 933,843, filed Nov. 24, 1986 and entitled Lancet Cartridge discloses a multiple use automatic surgical lancing device in which a series of separate lances are provided for sequential use in a single cartridge.

For definitional purposes in this document, a lance is a sharpened piece of stainless steel that pierces the skin. A lancet is a lance enclosed in a typically plastic housing to facilitate grasping the lance and loading it into a lancing device. A lancing device is a spring loaded mechanism that can be cocked and released to propel the lance forward for accurate and less traumatic puncturing of the skin. Lancing devices generally have a removable target piece adjacent the site of skin puncture called the platform which can become contaminated with body fluids during use. In contrast to single patient use, such as self testing by diabetics, situations arise where a care giver is drawing blood samples from multiple patients using a reusable lancing device, wherein the platform should be changed along with the lancet between patients to avoid any risk of cross contamination and the spread of infectious disease.

Unloading and loading lancets and changing platforms on reusable lancing devices is time consuming and costly. Frequently, to avoid this hassle, cost and risk, a care giver will merely hold the lancet and stab the patient's finger to draw a sample. This technique does not control depth of puncture and is painfully crude.

An integrated lancing device is a combination lance and lancing device in a typically single use disposable unit. The entire device may be discarded between patients and the time consuming steps of loading and unloading lancets and platforms is eliminated. Such devices as described in the above-referenced patents are generally not cost effective. It is a goal of this invention to provide the medical community with a cost effective integrated lancing device that can gain widespread usage and help stem the spread of infectious disease.

Since it is important for overall health reasons to use only sterile lancets and lancing devices in drawing blood, it is desirable that lancing devices used in a multiple patient situation, such as a blood bank, be reliably pre-sterilized during manufacture, used once, and then discarded. Thus, there is a strong need for the unit cost of such integrated surgical lancing devices to be reduced to a bare minimum. Also, patients on their own also need such a device.

In accordance with this invention a reliable, simplified type of integrated surgical lancing device is provided, being much smaller than previous designs and using much less plastic material than those of the prior art. However, the integrated lancing devices of this invention can perform functions equivalent to the lancing devices of the prior art, while having a significantly reduced unit cost and being significantly smaller, for desired space saving of the device when stored in bulk. The integrated lancing device of this invention is easily cocked and triggered, for successful patient use. Also, while desirably for one-time use, it is possible to use them on a repeated use basis, using alcohol sterilization of the lance or the like, if that becomes necessary.

DESCRIPTION OF THE INVENTION

In this invention, an integrated surgical lancing device is provided. The device comprises a generally U-shaped spring member defining a pair of arms having free ends. A lance is carried in transverse position on one of the arms adjacent the free end. The free end of the one arm typically defines a trigger projection positioned substantially along the axis of the one arm.

The other of the pair of arms carries a trigger member as an integral part thereof, the trigger member extending toward the trigger projection. As a result of this, the arms may be flexed outwardly into a cocked position, and held there by engagement of the trigger projection by the trigger member. The trigger member may then be manipulated to cause the arms to suddenly flex together, to cause the lance to strike a positioned body part of the patient.

By comparison with the prior art patents, it can be seen that the integrated lancing device of this invention utilizes much less plastic material and is of greatly simplified design. Specifically, the integrated lancing device may be free of side walls, and the trigger mechanism is greatly simplified with respect to the prior art.

The integrated lancing device of this invention may be substantially made of a single piece of molded plastic. The lance itself may constitute an integral part of the molded plastic, or a steel lance blade may be set into an aperture after the molding has taken place, as may be desired.

Preferably, the trigger member consists essentially of a single, straight, upstanding post positioned transversely to the other of the pair of arms from the one arm which carries the lance. The post carries a laterally projecting trigger arm capable of engaging the trigger projection, to hold the pair of arms in cocked position.

In one embodiment of this invention as specifically shown, the other of the pair of arms carries a handle member at a location remote from its free end, to strengthen that other arm and to facilitate grasping of the lancing device. Typically, the device of this invention is made so that the one arm is more flexible than the other arm, so that it is the one arm that mostly moves when they are flexed outwardly into the cocked position. This may be accomplished by making the one arm of less width than the other arm, and/or by making the one arm of less thickness than the other arm, as well as by use of the remote handle mentioned above.

The one arm may also carry a lifting handle adjacent its free end to assist in the cocking process.

In one embodiment of this invention, the other of the pair of arms defines adjacent its free end an outer platform defining a first aperture and an inner platform defining a second aperture. The inner platform is positioned within the first aperture, and is connected to the outer platform through a flexible connection member. Typically the outer and inner platforms are connected by only a single, flexible connection member on only one side of the inner platform, with the remainder of the inner platform being free and unconnected.

The trigger member is carried in a position to move with the flexing of the inner platform at the connection member. The lance is positioned to pass through the second aperture as the arms flex together. As a result of this, pressing with a body part of the inner platform of the integrated lancing device in cocked position causes the trigger member to release the trigger projection, and the lance to strike the body part.

It is particularly desirable in the embodiment described immediately above for the inner platform to project beyond the side of the other of the pair of arms, which side is opposed to the one arm. This facilitates pressing of the inner platform by a body part such as the finger, to trigger the spring contraction of the integrated lancing device and the drawing of a blood sample from the finger or the like.

Thus, the disagreeable task of drawing of blood samples is simplified and automated by the integrated lancing device of this invention, while the unit cost of such a device is significantly lower than the corresponding devices of the prior art.

DESCRIPTION OF THE DRAWINGS

Referring to the drawings.

FIG. 4 is an elevational view, with a portion broken away, of an alternate embodiment of the surgical lancing device of this invention, shown in cocked position;

FIG. 5 is an elevational view of the device of FIG. 4, showing it in its normal, unflexed position; and FIG. 6 is a fragmentary view taken along line 6—6 of FIG. 4.

DESCRIPTION OF SPECIFIC EMBODIMENTS

Figure 1:
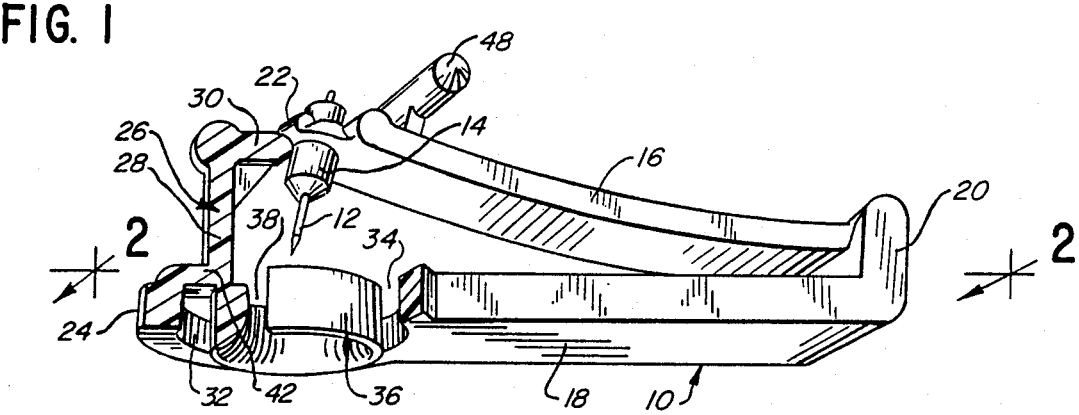
FIG. 1 is a perspective view, with a portion broken away, of one embodiment of the integrated surgical lancing device of this invention shown in cocked position.
Figure 2:
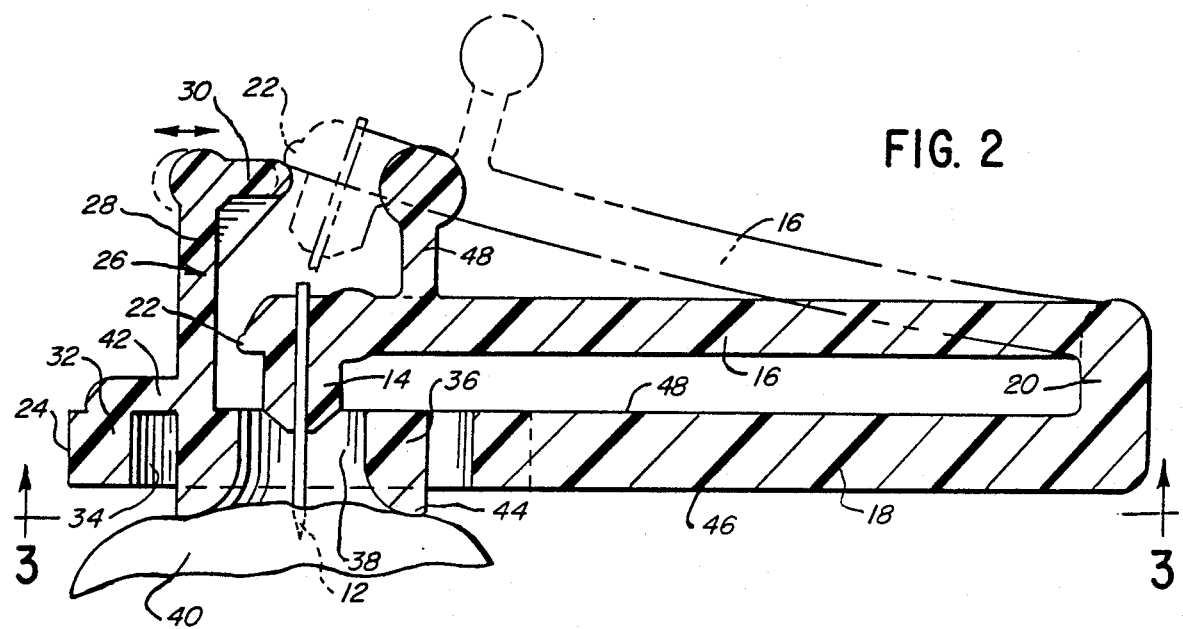
FIG. 2 is a longitudinal sectional view taken along line 2—2 of FIG. 1 but showing the device in normal, unflexed position.
Figure 3:
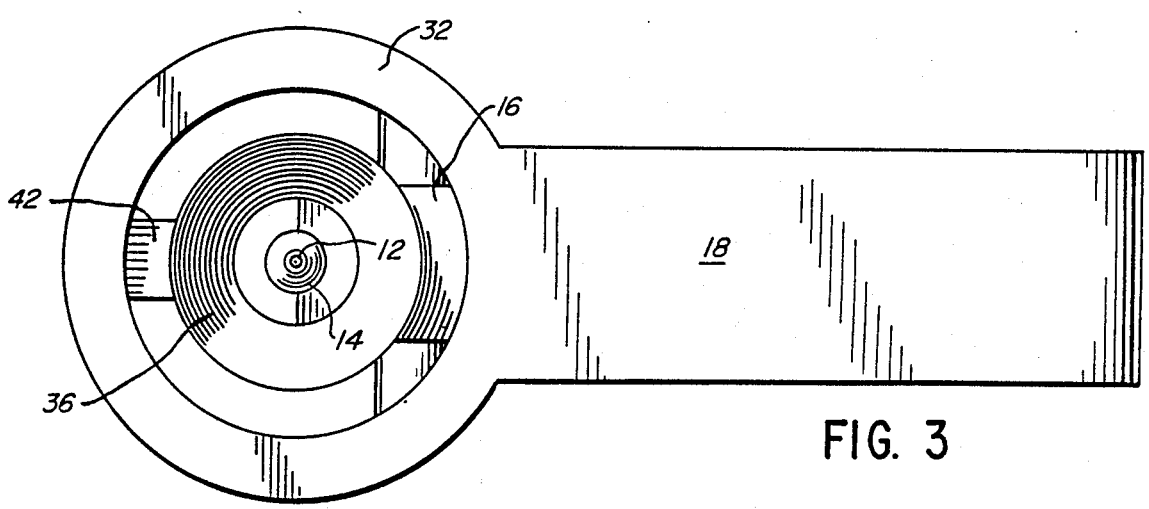
FIG. 3 is a bottom plan view of the device of FIG. 1 taken along line 3—3 of FIG. 3.

Referring to FIGS. 1 to 3, integrated surgical lancing device 10 is substantially made out of a single piece of molded plastic, with the exception of pointed, steel lance needle or blade 12, which in this embodiment may be set in a socket of needle holder 14 of the remainder of the one-piece plastic integrated lancing device 10.

Integrated lancing device 10 defines a pair of arms 16, 18, which are in generally U-shaped relation with each other and arm base 20 (the U-shaped arrangement of the arms and base being particularly shown in FIG. 2). Both of arms 16, 18 each define free ends 22, 24, with lance 12 and its holder 14 being carried in transverse position on first arm 16 at a position adjacent the free end 22 of such arm.

Free end 22 defines a trigger projection, as shown, which interacts with trigger member 26, carried adjacent free end 24 of second arm 18. Trigger member 26, as shown, extends toward trigger projection 22, and consists essentially of a single, straight, upstanding post 28 carrying a laterally projecting trigger arm 30 which is shown to engage trigger projection 22, to hold the pair of arms in cocked position as shown in FIG. 1. This simplified trigger member, which engages a trigger projection 22 at a position substantially along the axis of the one arm 16, provides a significantly simplified device of reduced manufacturing cost which is cheap enough for one-time use, but which may be reused if needed.

The second arm 18 defines, adjacent free end 24, a typically circular outer platform 32, which defines first aperture 34. It can be seen that the apertured outer platform 32 may be of other shapes as may be desired. Within aperture 34 there is positioned an inner platform 36, which also may be circular, or any other shape as desired. Inner platform 36 defines a second aperture 38, positioned so that lance 12 passes through aperture 38 to penetrate a finger 40 or other body part when released from its outwardly flexed, cocked position of FIG. 1, to snap back to its normal, unstressed position of FIG. 2.

Inner platform 36 is connected to outer platform 32 through a flexible connection member, specifically single, integral connection 42 which is a generally radially disposed bar as shown, connecting platform members 32, 36 together on only one side of inner platform 36. The remainder of inner platform 36 is free and unconnected about its periphery, as shown.

Thus, inner platform 36 is spring mounted with respect to the rest of integrated lancing device 10, so that pressure from finger 40 can flex it in a small angle of vertical rotation about connection bar 42. This is facilitated by the fact that inner platform 36 projects to a certain extent at area 44 beyond the side 46 of the other arm 18, which side is opposed to the side 48 that faces the one arm 16.

Trigger member 26 is carried in the vicinity of bar 42, so that as the finger flexes inner platform 36 as shown, upwardly, trigger member 26 rotates outwardly. By this, trigger projection 22 and trigger arm 30 can become separated while the lancet device 10 is in its cocked position as shown in FIG. 1, and also as shown in phantom in FIG. 2. Then, arm 16 snaps forcefully toward arm 18, driving lance 12 a short, predetermined distance into finger 40, for automated collection of a blood sample. It can be seen that this is accomplished merely by pressing inner platform 36 with the finger.

It can also be seen that first arm 16 is both of less width and thickness than second or other arm 18. Thus, most of the flexing motion takes place in arm 16 rather than arm 18.

Also, arm 16 may carry a lifting handle 48 adjacent its free end. This facilitates the manual cocking of the device prior to use.

Referring now to FIGS. 4 through 6, an alternate embodiment of integrated lancing device 10a is disclosed. The device operates on generally similar principles to those of the previous embodiment, but constitutes an even simpler embodiment. The generally U-shaped spring member defines first and second pair of arms 16a, 18a, as before, held together by base 20a. The one arm 16a carries a transversely disposed lance 12a by a socket 14a carried adjacent the free end of arm 16a. However, in this embodiment, if desired, the pointed lance blade 12a may be an integral part of the one-piece molded structure, being a pointed plastic shard of, for example the structure of an irregular pyramid, being integrally molded with the rest of integrated lancing device 10a.

As before, free end 22a of arm 16a defines a trigger projection, while a trigger member defines, as before, a straight, upstanding post 28a and a laterally projecting trigger arm 30a for engaging trigger projection 22a. Arm 16a may be both narrower in width and thickness than arm 18a so that most of the flexing takes place in arm 16a when the trigger member is placed in its cocked position, as shown in FIG. 4. Then, the exposed outer end 54 of trigger member 26a may be pulled outwardly by the fingers to disengage members 22a, 30a. Arm 16a snaps downwardly through aperture 38a, as shown in FIG. 5, to cause plastic lance 12a to penetrate finger 40 in a manner similar to that of the previous embodiment. As shown, arm 16a, while snapping inwardly, can overrun its normal position to an advanced position as shown in phantom, to penetrate finger 40, and then retract back to its normal, unstressed position in a spontaneous manner, so that lance blade 12a withdraws from the finger. The same overrunning principle may be used as desired in the first embodiment of FIGS. 1 and 3 as well.

Integrated lancing device 10a may be cocked by flexing first arm 16a outwardly, grasping horizontal lifting handle 48a to do so.

Thus, it can be seen that this second embodiment has parts that function in a manner similar to the corresponding parts of the previous embodiment, as illustrated by the corresponding reference numerals used herein.

Additionally, integrated lancing device 10a may define a handle member 50 carried on the other arm 18a at a location remote from its free end, to facilitate grasping of the integrated lancing device, and to provide more relative stiffness of arm 18a with respect to arm 16a.

Thus, by this invention, simplified, inexpensive, but reliable and easily used lancing devices are provided, inexpensive enough for one-time use, but reusable if that becomes necessary. The exposed lance 12, 12a in each case may be sterilized with alcohol, povidone iodine, or the like if reuse becomes necessary. The absence of sidewalls provides good access to the lance 12, 12a to permit manual sterilization thereof if necessary, and also to permit inspection of the device to be sure it is in working order.

The above has been offered for illustrative purposes only, and is not intended to limit the scope of the invention of this application, which is as defined in the claims below.

That which is claimed is:

1. An integrated lancing device which comprises:
a generally U-shaped spring member defining a pair of arms having free ends; a lance blade carried in transverse position on one of said arms adjacent said free end, the free end of said one arm defining a trigger projection positioned substantially along the axis of said one arm; the other of said pair of arms carrying a trigger member as an integral part thereof, said trigger member extending toward said trigger projection, whereby said arms may be flexed outwardly into a cocked position and held there by engagement of the trigger projection by the trigger member, and the trigger member may be manipulated to cause the arms to suddenly flex together to cause the lance blade to strike a positioned body part of a patient, the other of said pair of arms having a free end and defining, adjacent its free end, an outer platform defining a first aperture and an inner platform defining a second aperture, said inner platform being positioned within the first aperture and being connected to said outer platform through a flexible connection member, said trigger member being carried in a position to move with the flexing of the inner platform at said connection member, said lance blade being positioned to pass through the second aperture as the arms flex together, whereby pressing with the body part of the inner platform of the lancing device in cocked position causes the trigger member to release the trigger projection and the lance blade to strike said body part.

2. The integrated lancing device of claim 1 which is free of side walls.

3. The integrated lancing device of claim 1 in which said trigger member consists essentially of a single, straight, upstanding post positioned transversely to the other of said pair of arms, said post carrying a laterally projecting trigger arm capable of engaging said trigger projection to hold the pair of arms in cocked position.

4. The integrated lancing device of claim 1 in which said outer and inner platforms are of generally circular shape.

5. The integrated lancing device of claim 1 in which the outer and inner platforms are connected by a single connection member on only one side of the inner platform, the remainder of the inner platform being free and unconnected.

6. The integrated lancing device of claim 5 in which the inner platform projects beyond the side of the other of said pair of arms which is opposed to the one of said pair of arms, to facilitate said pressing by a body part.

7. The integrated lancing device of claim 1 in which said one of the pair of arms carries a lifting handle adjacent its free end.

8. The integrated lancing device of claim 1 in which said one of said pair of arms is more flexible than the other of said pair of arms.

9. An integrated lancing device which comprises: a generally U-shaped spring member defining a pair of arms having free ends; a lance blade carried in transverse position on one of said pair of arms adjacent said free end, and a trigger projection positioned on said one arm, the other of said pair of arms carrying a trigger member as an integral part thereof, said trigger member extending toward said trigger projection; the other of said pair of arms also defining, adjacent its free end, an outer platform defining a first aperture and an inner platform defining a second aperture, said inner platform being positioned within the first aperture and being connected to said outer platform through a flexible connection member, said trigger member being carried in a position to move with the flexing of the inner platform at said connection member, said lance blade being positioned to pass through the second aperture as the arms flex together, whereby said arms may be flexed outwardly into a cocked position and held there by engagement of the trigger projection by the trigger member, and pressing with a body part of the inner platform of the integrated lancing device in cocked position causes the trigger member to release the trigger projection, to cause the arms to suddenly flex together to cause the lancet to strike said body part.

10. The integrated lancing device of claim 9 in which the outer and inner platforms are connected by a single connection member only on one side of the inner platform, the remainder of the inner platform being free and unconnected.

11. The integrated lancing device of claim 10 in which the inner platform projects beyond the side of the other of said pair of arms which is opposed to the one of said pair of arms, to facilitate said pressing by a body part.

12. The integrated lancing device of claim 11 in which the one of said pair of arms is more flexible than the other of said pair of arms.

13. The integrated lancing device of claim 11 in which said outer and inner platforms are of generally circular shape.

14. The integrated lancing device of claim 11 in which said trigger member consists essentially of a single, straight, upstanding post positioned transversely to the other of said pair of arms, said post carrying a laterally projecting trigger arm capable of engaging said trigger projection to hold the pair of arms in cocked position.

15. The integrated lancing device of claim 11 which is substantially made of a single piece of molded plastic.

16. The integrated lancing device of claim 11 in which said one of the pair of arms carries a lifting handle adjacent its free end.

* * * * *